(12) United States Patent
Hammill, Sr. et al.

(10) Patent No.: US 7,942,909 B2
(45) Date of Patent: May 17, 2011

(54) THREAD-THRU POLYAXIAL PEDICLE SCREW SYSTEM

(75) Inventors: John E. Hammill, Sr., Maumee, OH (US); Robert L. Doubler, Monroe, MI (US)

(73) Assignee: Ortho Innovations, LLC, Palm Beach Gardens, FL (US)

( * ) Notice: Subject to any disclaimer, the term of this patent is extended or adjusted under 35 U.S.C. 154(b) by 145 days.

(21) Appl. No.: 12/540,398

(22) Filed: Aug. 13, 2009

(65) Prior Publication Data
US 2011/0040336 A1 Feb. 17, 2011

(51) Int. Cl.
*A61B 17/70* (2006.01)

(52) U.S. Cl. ...................... 606/267; 606/305

(58) Field of Classification Search .................. 606/246, 606/266–272, 279, 305–310
See application file for complete search history.

(56) References Cited

U.S. PATENT DOCUMENTS

| | | | |
|---|---|---|---|
| 3,433,510 A | 3/1969 | Hulterstrum |
| 4,273,116 A | 6/1981 | Chiquet |
| 4,419,026 A | 12/1983 | Leto |
| 4,483,334 A | 11/1984 | Murray |
| 4,570,982 A | 2/1986 | Blose et al. |
| 4,693,240 A | 9/1987 | Evans |
| 4,708,510 A | 11/1987 | McConnell et al. |
| 4,763,644 A | 8/1988 | Webb |
| 4,805,602 A | 2/1989 | Puno et al. |
| 4,836,196 A | 6/1989 | Park et al. |
| 4,841,959 A | 6/1989 | Ransford |
| 4,854,304 A | 8/1989 | Zielke |
| 4,867,144 A | 9/1989 | Karas et al. |
| 4,887,595 A | 12/1989 | Heinig et al. |
| 4,887,596 A | 12/1989 | Sherman |
| 4,946,458 A | 8/1990 | Harms et al. |
| 5,002,542 A | 3/1991 | Frigg |
| 5,005,562 A | 4/1991 | Cotrel |
| 5,084,049 A | 1/1992 | Asher et al. |
| 5,085,660 A | 2/1992 | Lin |
| 5,092,893 A | 3/1992 | Smith |
| 5,129,388 A | 7/1992 | Vignaud et al. |
| 5,129,900 A | 7/1992 | Asher et al. |
| 5,133,716 A | 7/1992 | Plaza |
| 5,133,717 A | 7/1992 | Chopin |
| 5,176,678 A | 1/1993 | Tsou |
| 5,207,678 A | 5/1993 | Harms et al. |
| 5,217,497 A | 6/1993 | Mehdian |
| 5,257,993 A | 11/1993 | Asher et al. |

(Continued)

FOREIGN PATENT DOCUMENTS
DE G9202745.8 4/1992
(Continued)

*Primary Examiner* — Thomas C Barrett
*Assistant Examiner* — Michael J Araj
(74) *Attorney, Agent, or Firm* — McHale & Slavin, P.A.

(57) ABSTRACT

A thread-thru polyaxial pedicle screw fastening system. The fastening system consists of an anchoring bone screw having threads on one end for use in anchoring to the screw to the spine and a spherical connector on the other end operating as a pivot point about which a U-shaped connecting assembly moves in a polyaxial fashion. The U-shaped connecting assembly, for receipt of a spinal connecting rod, has a biased retainer ring for maintaining a positive tension between the connecting assembly and the anchored screw. The system allows for an improved manufacturing step wherein the threaded shank of a bone screws can be passed through a lower portion of the connecting assembly allowing a variety of bone screw sizes to be used with a common sized connector.

16 Claims, 8 Drawing Sheets

U.S. PATENT DOCUMENTS

| | | |
|---|---|---|
| 5,261,909 A | 11/1993 | Sutterlin et al. |
| 5,261,912 A | 11/1993 | Frigg |
| 5,312,404 A | 5/1994 | Asher et al. |
| 5,312,405 A | 5/1994 | Korotko et al. |
| 5,330,477 A | 7/1994 | Crook |
| 5,360,431 A | 11/1994 | Puno et al. |
| 5,364,399 A | 11/1994 | Lowery et al. |
| 5,395,371 A | 3/1995 | Miller et al. |
| 5,429,639 A | 7/1995 | Judet |
| 5,437,671 A | 8/1995 | Lozier et al. |
| 5,443,467 A | 8/1995 | Biedermann et al. |
| 5,466,237 A | 11/1995 | Byrd, III et al. |
| 5,470,333 A | 11/1995 | Ray |
| 5,474,555 A | 12/1995 | Puno et al. |
| 5,476,462 A | 12/1995 | Allard et al. |
| 5,476,464 A | 12/1995 | Metz-Stavenhagen et al. |
| 5,480,401 A | 1/1996 | Navas |
| 5,496,321 A | 3/1996 | Puno et al. |
| 5,498,262 A | 3/1996 | Bryan |
| 5,498,263 A | 3/1996 | DiNello et al. |
| 5,501,684 A | 3/1996 | Schlapfer et al. |
| 5,520,690 A | 5/1996 | Errico et al. |
| 5,527,314 A | 6/1996 | Brumfield et al. |
| 5,531,746 A | 7/1996 | Errico et al. |
| 5,545,164 A | 8/1996 | Howland |
| 5,549,608 A | 8/1996 | Errico et al. |
| 5,554,157 A | 9/1996 | Errico et al. |
| 5,562,661 A | 10/1996 | Yoshimi et al. |
| 5,569,247 A | 10/1996 | Morrison |
| 5,575,792 A | 11/1996 | Errico et al. |
| 5,578,033 A | 11/1996 | Errico et al. |
| 5,584,834 A | 12/1996 | Errico et al. |
| 5,586,984 A | 12/1996 | Errico et al. |
| 5,591,165 A | 1/1997 | Jackson |
| 5,591,166 A | 1/1997 | Bernhardt et al. |
| 5,601,552 A | 2/1997 | Cotrel |
| 5,601,553 A | 2/1997 | Trebing et al. |
| 5,607,426 A | 3/1997 | Ralph et al. |
| 5,609,593 A | 3/1997 | Errico et al. |
| 5,609,594 A | 3/1997 | Errico et al. |
| 5,628,740 A | 5/1997 | Mullane |
| 5,643,261 A | 7/1997 | Schafer et al. |
| 5,643,265 A | 7/1997 | Errico et al. |
| 5,647,873 A | 7/1997 | Errico et al. |
| 5,669,910 A | 9/1997 | Korhonen et al. |
| 5,669,911 A | 9/1997 | Errico et al. |
| 5,672,176 A | 9/1997 | Biedermann et al. |
| 5,681,319 A | 10/1997 | Biedermann et al. |
| 5,688,272 A | 11/1997 | Montague et al. |
| 5,688,273 A | 11/1997 | Errico et al. |
| 5,690,630 A | 11/1997 | Errico et al. |
| 5,716,355 A | 2/1998 | Jackson et al. |
| 5,716,356 A | 2/1998 | Biedermann et al. |
| 5,716,357 A | 2/1998 | Rogozinski |
| 5,725,528 A | 3/1998 | Errico et al. |
| 5,725,588 A | 3/1998 | Errico et al. |
| 5,728,098 A | 3/1998 | Sherman et al. |
| 5,733,286 A | 3/1998 | Errico et al. |
| 5,738,685 A | 4/1998 | Halm et al. |
| 5,782,833 A | 7/1998 | Haider |
| 5,797,911 A | 8/1998 | Sherman et al. |
| 5,800,435 A | 9/1998 | Errico et al. |
| 5,810,818 A | 9/1998 | Errico et al. |
| 5,817,094 A | 10/1998 | Errico et al. |
| 5,863,293 A | 1/1999 | Richelsoph |
| 5,873,878 A | 2/1999 | Harms et al. |
| 5,876,402 A | 3/1999 | Errico et al. |
| 5,879,350 A | 3/1999 | Sherman et al. |
| 5,879,351 A | 3/1999 | Viart |
| 5,882,350 A | 3/1999 | Ralph et al. |
| 5,885,286 A | 3/1999 | Sherman et al. |
| 5,891,145 A | 4/1999 | Morrison et al. |
| 5,902,303 A | 5/1999 | Eckhof et al. |
| 5,947,966 A | 9/1999 | Drewry et al. |
| 5,954,725 A | 9/1999 | Sherman et al. |
| 5,961,517 A | 10/1999 | Biedermann et al. |
| 5,964,760 A | 10/1999 | Richelsoph |
| 5,980,523 A | 11/1999 | Jackson |
| 6,010,503 A | 1/2000 | Richelsoph et al. |
| 6,015,409 A | 1/2000 | Jackson |
| 6,019,759 A | 2/2000 | Rogozinski |
| 6,022,350 A | 2/2000 | Ganem |
| 6,050,997 A | 4/2000 | Mullane |
| 6,053,917 A | 4/2000 | Sherman et al. |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,080,156 A | 6/2000 | Asher et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,110,172 A | 8/2000 | Jackson |
| 6,113,600 A | 9/2000 | Drummond et al. |
| 6,113,601 A | 9/2000 | Tatar |
| 6,132,431 A | 10/2000 | Nilsson et al. |
| 6,132,432 A | 10/2000 | Richelsoph |
| 6,132,434 A | 10/2000 | Sherman et al. |
| 6,146,383 A | 11/2000 | Studer et al. |
| 6,183,472 B1 | 2/2001 | Lutz |
| 6,187,005 B1 | 2/2001 | Brace et al. |
| RE37,161 E | 5/2001 | Michelson et al. |
| 6,224,596 B1 | 5/2001 | Jackson |
| 6,248,105 B1 | 6/2001 | Schlapfer et al. |
| 6,254,602 B1 | 7/2001 | Justis |
| 6,261,287 B1 | 7/2001 | Metz-Stavenhagen |
| 6,273,888 B1 | 8/2001 | Justis |
| 6,280,442 B1 | 8/2001 | Barker et al. |
| 6,280,445 B1 | 8/2001 | Morrison et al. |
| 6,287,308 B1 | 9/2001 | Betz et al. |
| 6,287,311 B1 | 9/2001 | Sherman et al. |
| 6,296,642 B1 | 10/2001 | Morrison et al. |
| 6,302,888 B1 | 10/2001 | Mellinger et al. |
| 6,309,391 B1 | 10/2001 | Crandall et al. |
| 6,331,179 B1 | 12/2001 | Freid et al. |
| 6,355,040 B1 | 3/2002 | Richelsoph et al. |
| RE37,665 E | 4/2002 | Ralph et al. |
| 6,368,321 B1 | 4/2002 | Jackson |
| 6,383,190 B1 | 5/2002 | Preissman |
| 6,402,752 B2 | 6/2002 | Schaffler-Wachter et al. |
| 6,436,100 B1 | 8/2002 | Berger |
| 6,440,137 B1 | 8/2002 | Horvath et al. |
| 6,451,021 B1 | 9/2002 | Ralph et al. |
| 6,471,703 B1 | 10/2002 | Ashman |
| 6,471,705 B1 | 10/2002 | Biedermann et al. |
| 6,485,491 B1 | 11/2002 | Farris et al. |
| 6,485,494 B1 | 11/2002 | Haider |
| 6,488,681 B2 | 12/2002 | Martin et al. |
| 6,508,818 B2 | 1/2003 | Steiner et al. |
| 6,520,962 B1 | 2/2003 | Taylor et al. |
| 6,527,804 B1 | 3/2003 | Gauchet et al. |
| 6,530,929 B1 | 3/2003 | Justis et al. |
| 6,533,786 B1 | 3/2003 | Needham et al. |
| 6,537,276 B2 | 3/2003 | Metz-Stavenhagen |
| 6,547,789 B1 | 4/2003 | Ventre et al. |
| 6,547,790 B2 | 4/2003 | Harkey, III et al. |
| 6,551,320 B2 | 4/2003 | Lieberman |
| 6,554,832 B2 | 4/2003 | Shluzas |
| 6,554,834 B1 | 4/2003 | Crozet et al. |
| 6,558,387 B2 | 5/2003 | Errico et al. |
| 6,562,040 B1 | 5/2003 | Wagner |
| 6,565,565 B1 | 5/2003 | Yuan et al. |
| 6,565,567 B1 | 5/2003 | Haider |
| 6,582,436 B2 | 6/2003 | Schlapfer et al. |
| 6,582,466 B1 | 6/2003 | Gauchet |
| 6,585,740 B2 | 7/2003 | Schlapfer et al. |
| 6,595,992 B1 | 7/2003 | Wagner et al. |
| 6,595,993 B2 | 7/2003 | Donno et al. |
| 6,610,063 B2 | 8/2003 | Kumar et al. |
| 6,613,050 B1 | 9/2003 | Wagner et al. |
| 6,623,485 B2 | 9/2003 | Doubler et al. |
| 6,626,907 B2 | 9/2003 | Blain et al. |
| 6,626,908 B2 | 9/2003 | Cooper et al. |
| 6,635,059 B2 | 10/2003 | Randall et al. |
| 6,641,586 B2 | 11/2003 | Varieur |
| 6,648,885 B1 | 11/2003 | Friesem |
| 6,648,887 B2 | 11/2003 | Ashman |

| | | |
|---|---|---|
| 6,656,179 B1 | 12/2003 | Schaefer et al. |
| 6,656,181 B2 | 12/2003 | Dixon et al. |
| 6,660,004 B2 | 12/2003 | Barker et al. |
| 6,663,632 B1 | 12/2003 | Frigg |
| 6,663,635 B2 | 12/2003 | Frigg et al. |
| 6,672,788 B2 | 1/2004 | Hathaway |
| 6,673,073 B1 | 1/2004 | Schafer |
| 6,676,661 B1 | 1/2004 | Benlloch et al. |
| 6,679,833 B2 | 1/2004 | Smith et al. |
| 6,682,529 B2 | 1/2004 | Stahurski |
| 6,689,133 B2 | 2/2004 | Morrison et al. |
| 6,689,134 B2 | 2/2004 | Ralph et al. |
| 6,695,843 B2 | 2/2004 | Biedermann et al. |
| 6,695,851 B2 | 2/2004 | Zdeblick et al. |
| 6,699,249 B2 | 3/2004 | Schlapfer et al. |
| 6,706,045 B2 | 3/2004 | Lin et al. |
| 6,712,818 B1 | 3/2004 | Michelson |
| 6,716,213 B2 | 4/2004 | Shitoto |
| 6,716,214 B1 | 4/2004 | Jackson |
| 6,716,247 B2 | 4/2004 | Michelson |
| 6,723,100 B2 | 4/2004 | Biedermann et al. |
| 6,726,689 B2 | 4/2004 | Jackson |
| 6,730,093 B2 | 5/2004 | St. Martin |
| 6,730,127 B2 | 5/2004 | Michelson |
| 6,733,502 B2 | 5/2004 | Altarac et al. |
| 6,736,816 B2 | 5/2004 | Ritland |
| 6,736,820 B2 | 5/2004 | Biedermann et al. |
| 6,740,086 B2 | 5/2004 | Richelsoph |
| 6,746,449 B2 | 6/2004 | Jones et al. |
| 6,755,829 B1 | 6/2004 | Bono et al. |
| 6,755,830 B2 | 6/2004 | Minfelde et al. |
| 6,755,835 B2 | 6/2004 | Schultheiss et al. |
| 6,755,836 B1 | 6/2004 | Lewis |
| 6,761,723 B2 | 7/2004 | Buttermann et al. |
| 6,767,351 B2 | 7/2004 | Orbay et al. |
| 6,770,075 B2 | 8/2004 | Howland |
| 6,780,186 B2 | 8/2004 | Errico et al. |
| 6,790,209 B2 | 9/2004 | Beale et al. |
| 6,827,719 B2 | 12/2004 | Ralph et al. |
| 6,830,571 B2 | 12/2004 | Lenke et al. |
| 6,835,196 B2 | 12/2004 | Biedermann et al. |
| 6,837,889 B2 | 1/2005 | Shluzas |
| 6,840,940 B2 | 1/2005 | Ralph et al. |
| 6,843,791 B2 | 1/2005 | Serhan |
| 6,858,031 B2 | 2/2005 | Morrison et al. |
| 6,869,432 B2 | 3/2005 | Schlapfer et al. |
| 6,869,433 B2 | 3/2005 | Glascott |
| 6,872,208 B1 | 3/2005 | McBride et al. |
| 6,905,500 B2 | 6/2005 | Jeon et al. |
| 6,932,817 B2 | 8/2005 | Baynham et al. |
| 6,945,972 B2 | 9/2005 | Frigg et al. |
| 6,950,997 B2 | 9/2005 | Dickey et al. |
| 6,951,561 B2 | 10/2005 | Warren et al. |
| 6,953,462 B2 | 10/2005 | Lieberman |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,974,460 B2 | 12/2005 | Carbone et al. |
| 6,979,334 B2 | 12/2005 | Dalton |
| 6,981,973 B2 | 1/2006 | McKinley |
| RE39,035 E | 3/2006 | Finn et al. |
| 7,018,378 B2 | 3/2006 | Biedermann et al. |
| 7,018,379 B2 | 3/2006 | Drewry et al. |
| RE39,089 E | 5/2006 | Ralph et al. |
| 7,066,937 B2 | 6/2006 | Shluzas |
| 7,087,057 B2 | 8/2006 | Konieczynski et al. |
| 7,128,743 B2 | 10/2006 | Metz-Stavenhagen |
| 7,144,396 B2 | 12/2006 | Shluzas |
| 7,163,538 B2 | 1/2007 | Altarac et al. |
| 7,223,268 B2 | 5/2007 | Biedermann |
| 7,306,606 B2 | 12/2007 | Sasing |
| 7,322,981 B2 | 1/2008 | Jackson |
| 7,335,202 B2 | 2/2008 | Matthis et al. |
| 7,445,627 B2 | 11/2008 | Hawkes et al. |
| 7,604,656 B2 | 10/2009 | Shluzas |
| 7,682,377 B2 | 3/2010 | Konieczynski et al. |
| 2001/0001119 A1 | 5/2001 | Lombardo |
| 2002/0035366 A1 | 3/2002 | Walder et al. |
| 2002/0045898 A1 | 4/2002 | Freid et al. |
| 2002/0082602 A1 | 6/2002 | Biedermann et al. |
| 2002/0103487 A1 | 8/2002 | Errico et al. |
| 2002/0111626 A1 | 8/2002 | Ralph et al. |
| 2002/0143341 A1 | 10/2002 | Biedermann et al. |
| 2002/0173789 A1 | 11/2002 | Howland |
| 2002/0193795 A1 | 12/2002 | Gertzbein et al. |
| 2003/0004512 A1 | 1/2003 | Farris et al. |
| 2003/0023243 A1 | 1/2003 | Biedermann et al. |
| 2003/0045879 A1 | 3/2003 | Minfelde et al. |
| 2003/0073996 A1 | 4/2003 | Doubler et al. |
| 2003/0093078 A1 | 5/2003 | Ritland |
| 2003/0100896 A1 | 5/2003 | Biedermann et al. |
| 2003/0105460 A1 | 6/2003 | Crandall et al. |
| 2003/0118395 A1 | 6/2003 | Abels et al. |
| 2003/0125741 A1 | 7/2003 | Biedermann et al. |
| 2003/0149432 A1 | 8/2003 | Frigg et al. |
| 2003/0163133 A1 | 8/2003 | Altarac et al. |
| 2003/0176862 A1 | 9/2003 | Taylor et al. |
| 2003/0199873 A1 | 10/2003 | Richelsoph |
| 2003/0208204 A1 | 11/2003 | Bailey et al. |
| 2003/0216735 A1 | 11/2003 | Altarac et al. |
| 2004/0006342 A1 | 1/2004 | Altarac et al. |
| 2004/0024464 A1 | 2/2004 | Errico et al. |
| 2004/0092934 A1 | 5/2004 | Howland |
| 2004/0097933 A1 | 5/2004 | Lourdel et al. |
| 2004/0102781 A1 | 5/2004 | Jeon |
| 2004/0116929 A1 | 6/2004 | Barker et al. |
| 2004/0127906 A1 | 7/2004 | Culbert et al. |
| 2004/0138662 A1 | 7/2004 | Landry et al. |
| 2004/0143265 A1 | 7/2004 | Landry et al. |
| 2004/0147929 A1 | 7/2004 | Biedermann et al. |
| 2004/0158247 A1 | 8/2004 | Sitiso et al. |
| 2004/0172022 A1 | 9/2004 | Landry et al. |
| 2004/0176766 A1 | 9/2004 | Shluzas |
| 2004/0181224 A1 | 9/2004 | Biedermann et al. |
| 2004/0186473 A1 | 9/2004 | Cournoyer et al. |
| 2004/0193160 A1 | 9/2004 | Richelsoph |
| 2004/0210216 A1 | 10/2004 | Farris et al. |
| 2004/0225289 A1 | 11/2004 | Biedermann et al. |
| 2004/0236330 A1 | 11/2004 | Purcell et al. |
| 2004/0249380 A1 | 12/2004 | Glascott |
| 2004/0267264 A1 | 12/2004 | Konieczynski et al. |
| 2005/0027296 A1 | 2/2005 | Thramann et al. |
| 2005/0033289 A1 | 2/2005 | Warren et al. |
| 2005/0055026 A1 | 3/2005 | Biedermann et al. |
| 2005/0070899 A1 | 3/2005 | Doubler et al. |
| 2005/0080415 A1 | 4/2005 | Keyer et al. |
| 2005/0107788 A1 | 5/2005 | Beaurain et al. |
| 2005/0113927 A1 | 5/2005 | Malek |
| 2005/0131404 A1 | 6/2005 | Mazda et al. |
| 2005/0131409 A1 | 6/2005 | Chervitz et al. |
| 2005/0131413 A1 | 6/2005 | O'Driscoll et al. |
| 2005/0131537 A1 | 6/2005 | Hoy et al. |
| 2005/0131538 A1 | 6/2005 | Chervitz et al. |
| 2005/0131545 A1 | 6/2005 | Chervitz et al. |
| 2005/0149023 A1 | 7/2005 | Ritland |
| 2005/0154389 A1 | 7/2005 | Selover et al. |
| 2005/0154391 A1 | 7/2005 | Doherty et al. |
| 2005/0159750 A1 | 7/2005 | Doherty |
| 2005/0165400 A1 | 7/2005 | Fernandez |
| 2005/0171540 A1 | 8/2005 | Lim et al. |
| 2005/0187548 A1 | 8/2005 | Butler et al. |
| 2005/0187555 A1 | 8/2005 | Biedermann et al. |
| 2005/0192571 A1 | 9/2005 | Abdelgany |
| 2005/0192580 A1 | 9/2005 | Dalton |
| 2005/0203515 A1 | 9/2005 | Doherty et al. |
| 2005/0203516 A1 | 9/2005 | Biedermann et al. |
| 2005/0216003 A1 | 9/2005 | Biedermann et al. |
| 2005/0228392 A1 | 10/2005 | Keyer et al. |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0240181 A1 | 10/2005 | Boomer et al. |
| 2005/0240183 A1 | 10/2005 | Vaughan |
| 2005/0251137 A1 | 11/2005 | Ball |
| 2005/0251141 A1 | 11/2005 | Frigg et al. |
| 2005/0261687 A1 | 11/2005 | Garamszegi et al. |

| | | |
|---|---|---|
| 2005/0267474 A1 | 12/2005 | Dalton |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277925 A1 | 12/2005 | Mujwid |
| 2005/0277928 A1 | 12/2005 | Boschert |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0288669 A1 | 12/2005 | Abdou |
| 2005/0288671 A1 | 12/2005 | Yuan et al. |
| 2005/0288673 A1 | 12/2005 | Catbagan et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brockmeyer et al. |
| 2006/0009769 A1 | 1/2006 | Lieberman |
| 2006/0009770 A1 | 1/2006 | Speirs et al. |
| 2006/0015104 A1 | 1/2006 | Dalton |
| 2006/0015105 A1 | 1/2006 | Warren et al. |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0036242 A1 | 2/2006 | Nilsson et al. |
| 2006/0036252 A1 | 2/2006 | Baynham et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0084981 A1 | 4/2006 | Shluzas |
| 2006/0149240 A1 | 7/2006 | Jackson |
| 2006/0149241 A1 | 7/2006 | Richelsoph et al. |
| 2006/0155277 A1 | 7/2006 | Metz-Stavenhagen |
| 2006/0235392 A1 | 10/2006 | Hammer et al. |
| 2006/0241599 A1 | 10/2006 | Konieczynski et al. |
| 2006/0241600 A1 | 10/2006 | Ensign et al. |
| 2006/0241603 A1 | 10/2006 | Jackson |
| 2006/0276791 A1 | 12/2006 | Shluzas |
| 2006/0293665 A1* | 12/2006 | Shluzas ............ 606/61 |
| 2007/0055241 A1 | 3/2007 | Matthis et al. |
| 2007/0093818 A1 | 4/2007 | Biedermann et al. |
| 2007/0093826 A1 | 4/2007 | Hawkes et al. |
| 2007/0118132 A1 | 5/2007 | Culbert et al. |
| 2007/0123868 A1 | 5/2007 | Culbert et al. |
| 2007/0161996 A1 | 7/2007 | Biedermann et al. |
| 2007/0161999 A1 | 7/2007 | Biedermann et al. |
| 2007/0219556 A1 | 9/2007 | Altarac et al. |
| 2007/0225712 A1 | 9/2007 | Altarac et al. |
| 2007/0225713 A1 | 9/2007 | Altarac et al. |
| 2007/0270813 A1 | 11/2007 | Garamszegi |
| 2008/0009862 A1* | 1/2008 | Hoffman ............ 606/61 |
| 2008/0015576 A1 | 1/2008 | Whipple |
| 2008/0015579 A1 | 1/2008 | Whipple |
| 2008/0015580 A1 | 1/2008 | Chao |
| 2008/0015597 A1 | 1/2008 | Whipple |
| 2008/0045953 A1 | 2/2008 | Garamszegi |
| 2008/0097436 A1 | 4/2008 | Culbert et al. |
| 2008/0177322 A1 | 7/2008 | Davis et al. |
| 2008/0269809 A1 | 10/2008 | Garamszegi |
| 2008/0287998 A1 | 11/2008 | Doubler et al. |
| 2009/0163956 A1 | 6/2009 | Biedermann et al. |

FOREIGN PATENT DOCUMENTS

| | | |
|---|---|---|
| DE | 19509332 | 8/1996 |
| DE | 19507141 | 9/1996 |
| DE | 19720782 | 12/2004 |
| EP | 1121902 | 8/2001 |
| EP | 1190678 | 3/2002 |
| EP | 1474050 | 11/2004 |
| EP | 1570795 | 9/2005 |
| EP | 1579816 | 9/2005 |
| EP | 1634537 | 3/2006 |
| FR | 2729291 | 7/1996 |
| FR | 2796545 | 1/2001 |
| FR | 2856578 | 6/2003 |
| FR | 2865373 | 1/2004 |
| FR | 2865375 | 1/2004 |
| FR | 2865377 | 1/2004 |
| FR | 2857850 | 4/2004 |
| FR | 2865378 | 10/2004 |
| GB | 2173104 | 10/1986 |
| GB | 2365345 | 2/2002 |
| WO | WO01/49191 | 7/2001 |
| WO | WO02/054966 | 7/2002 |
| WO | WO03/068088 | 8/2003 |
| WO | WO03068083 | 8/2003 |
| WO | WO2004/041100 | 5/2004 |
| WO | WO2004/089245 | 10/2004 |
| WO | WO2004/107997 | 12/2004 |
| WO | WO2005/000136 | 1/2005 |
| WO | WO2005/000137 | 1/2005 |
| WO | WO2005/020829 | 3/2005 |
| WO | WO2005/072632 | 8/2005 |
| WO | WO2005/082262 | 9/2005 |
| WO | WO2005/099400 | 10/2005 |
| WO | WO2006/012088 | 2/2006 |
| WO | WO2006/017616 | 2/2006 |
| WO | WO2006/028537 | 3/2006 |

* cited by examiner

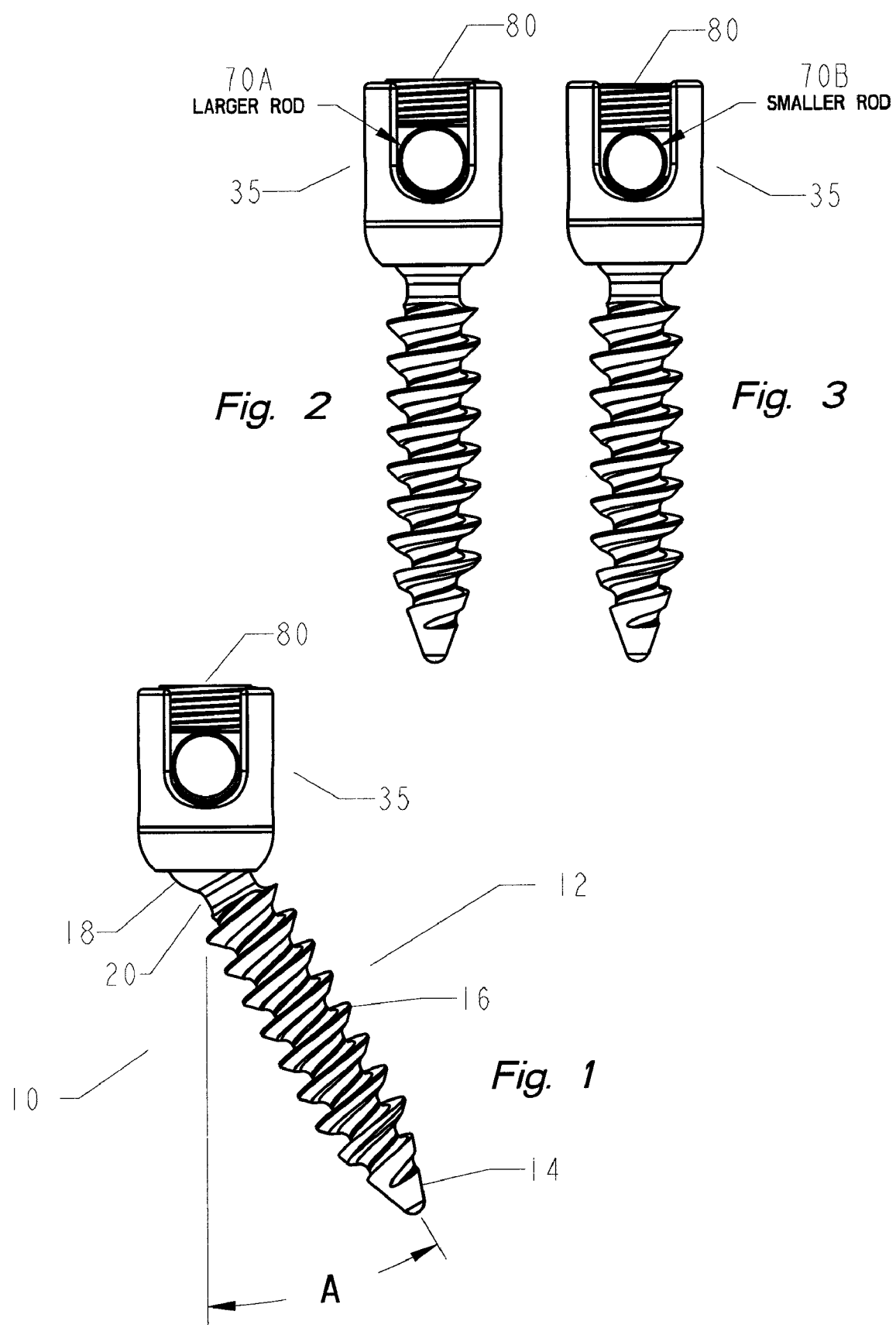

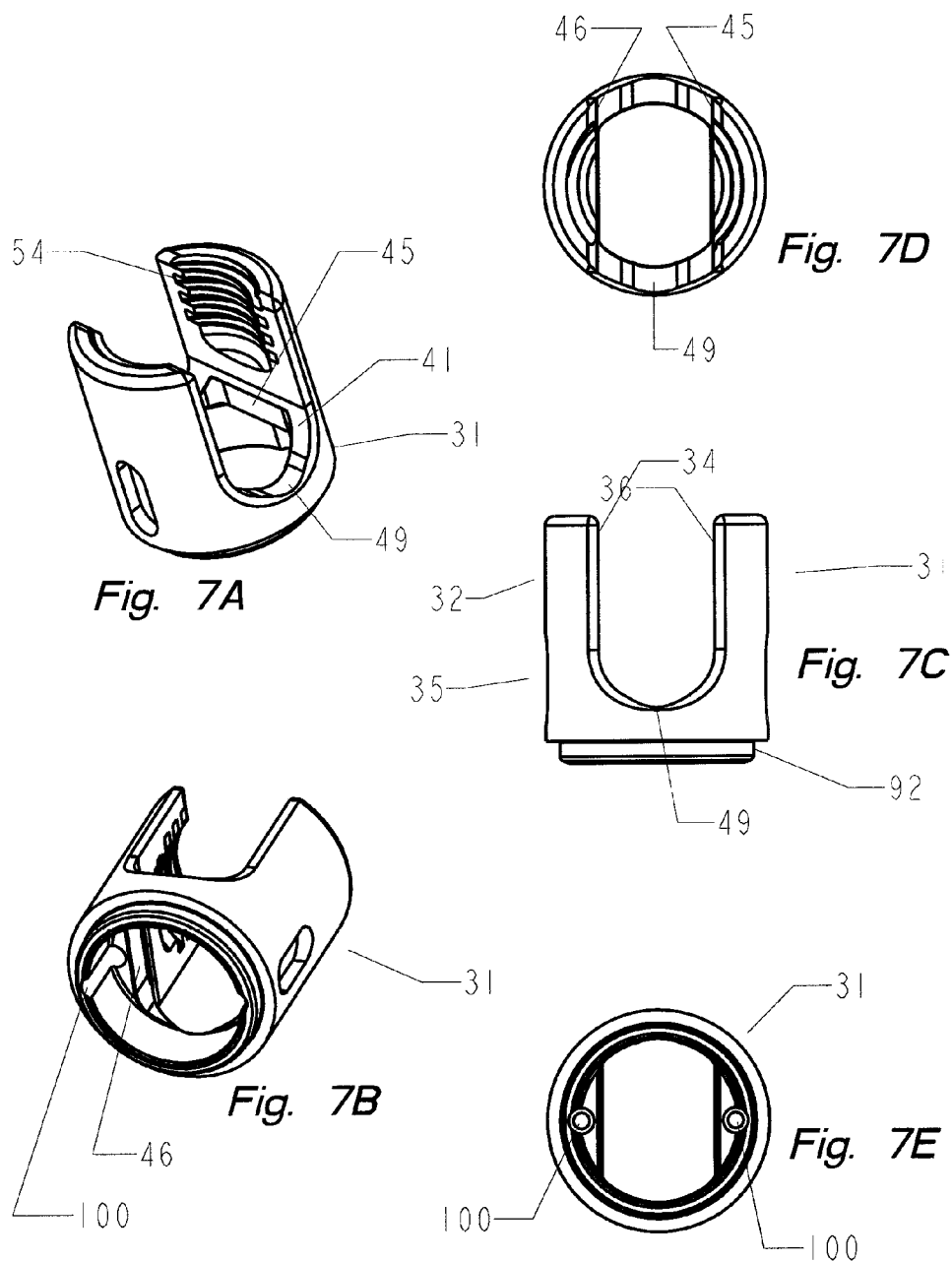

THREAD-THRU POLYAXIAL PEDICLE SCREW SYSTEM

CROSS REFERENCE TO RELATED APPLICATIONS

This application is related to U.S. patent application Ser. No. 12/355,145 filed Jan. 16, 2009 which claims the benefit of the filing date of U.S. Provisional Patent Application No. 61/114,515 filed on Nov. 14, 2008; and U.S. patent application Ser. No. 11/749,615 filed May 16, 2007 the contents of these applications are herein incorporated by reference.

FIELD OF THE INVENTION

This invention is directed to the field of pedicle screws, and in particular, to a thread-thru polyaxial pedicle screw system adapted for use as a spinal implant.

BACKGROUND OF THE INVENTION

The use of pedicle screw fasteners is well known for their use with spinal fixation systems. In the field of spinal pathologies, spinal fixation systems represent a major medical breakthrough. Surgically implanted fixation systems are commonly used to correct a variety of back structure problems, including those which occur as a result of trauma or improper development during growth. A commonly applied fixation system includes the use of one or more stabilizing rods aligned in a desired orientation with respect to a patient's spine. The pedicle screw provides anchoring of the fixation system wherein a series of connectors are used to rigidly link rods and the anchors.

Common to all spinal implant systems is the necessity for proper anchoring to the bone so as to provide support for the aforementioned components. The use of a polyaxial design pedicle screw has proven very effective in allowing a surgeon the flexibility to secure an installation with minimal strain on the individual. However, one of the problems with a polyaxial pedicle screw is the lack of a stabilized angular placement position during installation. Once a polyaxial pedicle screw is inserted into the bone, the connector component portion has yet to receive a connecting rod leaving the connector assembly to flop over making it difficult for the Surgeon to grasp while in the midst of surgery. This problem is compounded by the need to align multiple component heads for receipt of a connecting rod. Another problem with the prior art is the inability to use various size anchoring screw in combination with a common saddle larger saddle, both of which leads to assembly integrity over a large range of installation considerations.

A conventional polyaxial bone screw typically consists of a single shaft with a coarse thread at one end for threading into the bone. A spherical ball is positioned at an opposite end for coupling to a connecting member. For example, a number of patents exist for bone screw anchoring assemblies that include a U-shaped connector element which acts as a saddle for attachment to an alignment rod. U.S. Pat. No. 5,133,717 sets forth a sacral screw with a saddle support. Disclosed is the use of an auxiliary angled screw to provide the necessary support in placing the screw in an angular position for improved anchoring.

U.S. Pat. No. 5,129,900 sets forth an attachment screw and connector member that is adjustably fastened to an alignment rod. An oblong area provided within each connector member allows minute displacement of the alignment rod.

U.S. Pat. No. 4,887,595 discloses a screw that has a first externally threaded portion for engagement with the bone and a second externally threaded portion for engagement with a locking nut. The disclosure illustrates the use of a singular fixed shaft.

U.S. Pat. No. 4,946,458 discloses a screw which employs a spherical portion which is adapted to receive a locking pin so as to allow one portion of the screw to rotate around the spherical portion. A problem with the screw is the need for the locking pin and the inability of the base screw to accommodate a threaded extension bolt.

U.S. Pat. No. 5,002,542 discloses a screw clamp wherein two horizontally disposed sections are adapted to receive the head of a pedicle screw for use in combination with a hook which holds a support rod at an adjustable distance.

U.S. Pat. No. 4,854,304 discloses the use of a screw with a top portion that is adaptable for use with a specially designed alignment rod to permit compression as well as distraction.

U.S. Pat. No. 4,887,596 discloses a pedicle screw for use in coupling an alignment rod to the spine wherein the screw includes a clamp permitting adjustment of the angle between the alignment rod and the screw.

U.S. Pat. No. 4,836,196 discloses a screw with an upper portion designed for threadingly engaging a semi-spherical cup for use with a specially designed alignment rod. The alignment rod includes spaced apart covertures for receipt of a spherical disc allowing a support rod to be placed at angular positions.

U.S. Pat. No. 5,800,435 sets forth a modular spinal plate assembly for use with polyaxial pedicle screw implant devices. The device includes compressible components that cooperatively lock the device along included rails.

U.S. Pat. No. 5,591,166 discloses an orthopedic bone bolt and bone plate construction including a bone plate member and a collection of fasteners. At least one of the fasteners allows for multi-angle mounting configurations. The fasteners also include threaded portions configured to engage a patient's bone tissue.

U.S. Pat. No. 5,569,247 discloses a multi-angle fastener usable for connecting patient bone to other surgical implant components. The '247 device includes fastening bolts having spherical, multi-piece heads that allow for adjustment during installation of the device.

U.S. Pat. No. 5,716,357 discloses a spinal treatment and long bone fixation apparatus. The apparatus includes link members adapted to engage patient vertebrae. The link members may be attached in a chain-like fashion to connect bones in a non-linear arrangement. The apparatus also includes at least one multi-directional attachment member for joining the link members. This allows the apparatus to be used in forming a spinal implant fixation system.

Another type of spinal fixation system includes rigid screws that engage the posterior region of a patient's spine. The screws are designed with rod-engaging free ends to engage a support rod that has been formed into a desired spine-curvature-correcting orientation. Clamping members are often used to lock the rod in place with respect to the screws. Instead of clamping members, other fixation systems, such as that disclosed in U.S. Pat. No. 5,129,900 employs connectors that join the support rods and anchoring screws. The connectors eliminate unwanted relative motion between the rod and the screws, thereby maintaining the patient's spine in a corrected orientation.

Other spinal fixation systems employ adjustable components. For example, U.S. Pat. No. 5,549,608 includes anchoring screws that have pivoting free ends which attach to discrete rod-engaging couplers. As a result, the relative position of the anchoring screws and rods may be adjusted to achieve a proper fit, even after the screw has been anchored into a patient's spinal bone. This type of fixation system succeeds in easing the rod-and-screw-linking process. This adjustment capability allows the screws to accommodate several rod paths.

U.S. Pat. No. 7,445,627 discloses a fastener and a bone fixation assembly for internal fixation of vertebral bodies. According to one exemplary embodiment, a tulip assembly is employed; the tulip assembly includes a non-circular surface disposed on its outer surface. A fastener is coupled to the tulip assembly and positionable to retain the tulip assembly on the head of a screw. A cap having an outer surface and a plurality of inner protrusions mateably connects to the non-circular surface on the tulip body to compress the tulip assembly to secure a rod.

U.S. Publication No. 2008/0177322 discloses a spinal stabilization system that includes bone fastener assemblies that are coupled to vertebrae. Each bone fastener assembly includes a bone fastener and a collar. The bone fastener has a head portion having at least a first cross-sectional shape in a first plane, and a second cross-sectional shape in a second plane. The collar has a circular opening in the bottom, with a relief extending from the circular opening. The second cross-sectional shape of the bone fastener is keyed to the opening to permit insertion of the bone fastener into the collar assembly from the bottom. After insertion, the bone fastener is rotated to prohibit removal of the bone fastener from the collar. The collar can then be rotated and/or angulated relative to the bone fastener. An elongated member can be positioned in the collar and a closure member is then used to secure the elongated member to the collar.

U.S. Publication No. 2006/0241599 discloses a polyaxial fixation device having a shank with a spherical head formed on a proximal end thereof, and a receiver member having an axial passage formed therein that is adapted to polyaxially seat the spherical head of the shank. The polyaxial bone screw further includes an engagement member that is adapted to provide sufficient friction between the spherical head and the receiver member to enable the shank to be maintained in a desired angular orientation before locking the spherical head within the receiver member.

U.S. Publication No. 2006/0235392 discloses a system for connecting a fastener element (e.g., a pedicle screw) relative to a rod for the purposes of vertebral fixation. The system may permit multi-axial movement between the fastener element and the rod. Further, the system may permit the angular relationship between the fastener element and the rod to be held in a desired orientation.

U.S. Publication No. 2006/0155277 discloses an anchoring element for securing a rod on a vertebra, that comprises a retaining means for receiving the rod, a safety element placed on the retaining means, a securing element which can be placed on the body of the vertebra, and a clamping device which is arranged between the retaining means and the securing element. The clamping device includes a ring-shaped mount, a partially conical-segment shaped bearing and an intermediate element which is embedded in the mount and which engages the bearing, whereby the mounting is moveable in a removed state in relation to the bearing, whereas the mount is maintained in a clamped state on the bearing by means of the intermediate element. The mount is rigidly connected to the retaining means and the bearing is rigidly connected to the securing element.

U.S. Publication No. 2006/0149240 discloses a polyaxial bone screw assembly that includes a threaded shank body having an upper capture structure, a head and a multi-piece retainer, articulation structure. The geometry of the retainer structure pieces correspond and cooperate with the external geometry of the capture structure to frictionally envelope the retainer structure between the capture structure and an internal surface defining a cavity of the head. The head has a U-shaped cradle defining a channel for receiving a spinal fixation or stabilization longitudinal connecting member. The head channel communicates with the cavity and further with a restrictive opening that receives retainer pieces and the capture structure into the head but prevents passage of frictionally engaged retainer and capture structures out of the head. The retainer structure includes a substantially spherical surface that mates with the internal surface of the head, providing a ball joint, enabling the head to be disposed at an angle relative to the shank body.

U.S. Pat. No. 6,716,214 discloses a polyaxial bone screw having a bone implantable shank, a head and a retaining ring. The retaining ring includes an outer partial hemispherical surface and an inner bore with radially extending channels and partial capture recesses. The shank includes a bone implantable body with an external helical wound thread and an upwardly extending capture structure. The capture structure includes at least one spline which extends radially outward and has a wedged surface that faces radially outward therefrom. The capture structure operably passes through a central bore of the retaining ring while the spline passes through a suitably shaped channel so that the spline becomes positioned above the head, at which time the shank is rotated appropriately and the shank is drawn back downwardly so that the spline engages and seats in the capture recess. The head includes an internal cavity having a spherical shaped surface that mates with the ring surface and has a lower restrictive neck that prevents passage of the ring once the ring is seated in the cavity.

U.S. Pat. No. 6,565,567 discloses a pedicle screw assembly for use with a rod for the immobilization of bone segments. The assembly is comprised of a screw, a polyaxial housing for receiving the screw, a washer, a set screw, and a cup-shaped cap. The lower portion of the housing terminates in a reduced cross-sectional area, which engages the bottom of the screw head. When the screw is placed inside the polyaxial housing and the screw is secured into the bone, the polyaxial housing is pivotable with three degrees of freedom. The housing includes a top portion with a pair of upstanding internally threaded posts. A washer is inserted between the head of the screw and the rod. A cap, having a bottom, with a pair of posts accommodating openings and a lateral cross connector, is placed over the posts so that the cross connector engages the rod. The cross connector and washer have concave generally semi-cylindrical rod engaging surfaces to prevent the rod from rotating or sliding within the housing once the set screw is tightened. A set screw is threaded into the housing posts to secure the rod within the housing. The washer has a roughened lower surface which, in conjunction with the reduced cross-sectional area at the bottom of the housing, securely clamps and locks the housing to the screw head when the set screw is tightened.

U.S. Pat. No. 5,501,684 discloses an osteosynthetic fixation device which consists of a fixation element which has a conical head section and an anchoring element abutting it which is for attachment into the bone. The fixation device also consists of a spherically formed, layered, slotted clamping piece which has a conical borehole for installation of the conical head section, and which is meant for locking within a connecting piece equipped with a spherically shaped layered borehole. Fixation piece has an axially arrayed tension element, permitting axial displacement and wedging of conical head section in the borehole that corresponds with it. The fixation device is appropriate for use as a plate/screw system, an internal or external fixator, and in particular for spinal column fixation.

U.S. Pat. No. 4,693,240 discloses a bone pin clamp for external fracture fixation. The apparatus comprises rotation, slide and housing elements nested one within the next, each such element having an aperture to receive a pin therethrough, and the rotation and slide elements respectively affording pin adjustment in azimuth and zenith, and in height, relative to the housing element. A locking mechanism including a common actuator member is operable simultaneously to lock the pin and rotation and slide elements in the housing element. In a preferred form, the housing element serves as a cylinder with the slide element as a keyed piston therein, and the rotation element is a disc located between a screw and annular thrust members engaged in the piston, the piston and disc being split respectively to lock by expansion and compaction under screw action towards the thrust members.

U.S. Pat. No. 4,483,334 discloses an external fixation device for holding bone segments in known relation to each other. The device includes a pair of bone clamp assemblies each secured to bone pins extending from the bone segments, a bridge extending between the pin clamp assemblies, and a specialized high friction universal assembly connecting the bridge to each of the pin clamp assemblies.

U.S. Pat. No. 4,273,116 discloses an external fixation device for reducing fractures and realigning bones that includes sliding universal articulated couplings for enabling easy adjustment and subsequent locking of connections between Steinmann pins and tubular tie-rods. The couplings each include a split, spherical adapter sleeve which is embraced by the matching inner surface of an open ring portion of a coupling locking clamp having clamp lugs tightenable against a block by means of a nut-and-bolt assembly. Further nut-and-bolt assemblies are disposed in elongated slots in the blocks and cooperate with associated clamping members to clamp the Steinmann pins to the blocks after adjustment in two orthogonal directions and optional resilient bending of the pins.

U.S. Pat. No. 6,672,788 discloses a ball and socket joint incorporating a detent mechanism that provides positive biasing toward a desired position. The ball and socket joint can be used in flexible supports that hold and support items such as lamps, tools and faucets. The detent mechanism comprises two corresponding parts, one in the ball portion and the second in the socket portion of the joint. The first detent part is a protrusion of some type and the second detent part is a groove or indentation that is adapted to accept and engage the protrusion. If the ball contains the detent protrusion, then the socket contains the detent indentation. And conversely, if the socket contains the detent protrusion, then the ball contains the detent indentation. The detent tensioning force can be provided by a spring or a spring band, the characteristics of the material from which the joint is made, or by some other similar tensioning device.

U.S. Publication No. 2003/0118395 discloses a ball and socket joint, which has a housing, a ball pivot mounted pivotably in the housing, and a sealing bellows, which is fastened to the housing and is mounted on the ball pivot slidably via a sealing ring provided with two legs. A first leg of the two legs is in contact with the ball pivot under tension and the second leg meshes with the wall of the sealing bellows. The second leg is, furthermore, fastened in an anchoring ring arranged at least partially in the wall of the sealing bellows.

U.S. Pat. No. 4,708,510 discloses a ball joint coupling assembly that permits universal movement and positioning of an object with respect to a vertical support shaft. Quick release/lock action is provided by a ball joint assembly having a housing in which a ball and piston are movably coupled. The ball is captured between annular jaw portions of the housing and piston, with locking action being provided by gripping engagement of the piston jaw portion and the housing jaw portion. The ball member is gripped in line-contact, compressive engagement by the annular edges of the piston jaw and housing jaw on opposite sides of the ball. The piston is constrained for axial movement within the housing with locking engagement and release being effected by rotation of a threaded actuator shaft.

U.S. Pat. No. 3,433,510 discloses a swivel structure for rigidly joining first and second parts together. A first member is connected to the first part and a second member is connected to the second part. An intermediate hollow member interconnects the first and second members together. An enlarged outer end portion is provided on the first member and includes a plurality of locking means thereon. Means are provided on the second member for engaging one of the locking means. Means are provided for threadably joining the hollow member and the second member together. A slot is provided in the hollow member and includes an enlarged entrance which passes the enlarged outer end portion and which also includes a restricted opening opposite the threaded joining of the hollow member and the second member together. The portion surrounding the restricted opening opposes the forces imparted against the outer end portion as the second member is threadably joined to the hollow portion and bears against the outer end portion.

U.S. Patent Publication No. 2008/0269809 discloses a bottom loading pedicle screw assembly. The device includes a pedicle screw and a connector member. The pedicle screw includes a threaded lower portion while the upper portion includes a groove sized to accept a clip member. The clip member includes a spherical outer surface. In operation the clip is placed within the groove and the assembly is pressed through the opening in the bottom of the connector member. While the device is bottom loading, the device will separate when the pedicle screw is aligned with the connector member. The construction of the clip member allows the clip to collapse sufficiently to pass back through the opening when the screw is positioned in alignment with the connector, requiring the connection to bone be placed at an angle with respect to the connector for proper operation.

Thus, what is needed is a polyaxial pedicle screw system that can be adapted for use in a spinal fixation system that includes a thread thru assembly allowing different sized anchoring screws to be coupled to a single size connector, and an assembly that maintains the connector member in position to assist a surgeon during installation.

SUMMARY OF THE INVENTION

The present invention is a polyaxial pedicle screw system that permits the threads of a pedicle screw to pass thru a lower section of a connecting member during manufacturing. The pass thru design permits the manufacturer to use a range of different size shanks and threads while using a common connector member thereby lowering inventory costs and providing the surgeon with a similar shaped connector despite the type of pedicle screw employed. The system includes a means for applying tension to the pedicle screw anchoring member to assist in surgery.

The polyaxial bone screw has a threaded shank extending outwardly from a spherical ball for use in anchoring to the spine and a connector member that includes a socket constructed and arranged to accept the spherical ball. In the disclosed embodiment, the connector member is illustrated as a U-shaped connector member having a lower receptacle that operates as a socket for housing a retainer ring. The socket is receptive to the spherical ball which is inserted through the top of the connector during a manufacturing step. The retainer ring is spring loaded against a upper component of the connector member and engages the spherical ball so as to keep the U-shaped connector member in position during installation. A surgeon can easily move the connector member into a preferred position and the springs keep sufficient tension on the retainer ring so as to maintain the connector in position. This facilitates the installation of the rod as the U-shaped connector not only can be rotated into a position for proper placement of the connecting rod but the proper angle of the saddle can also maintained allowing the surgeon to align additional screws for ease of rod placement, and bend the rod as needed to align for any office anchoring.

A fastener member, such as a set screw or nut, is utilized to press the retaining ring into contact with the spherical ball while simultaneously causing a lower portion of the ball to engage the inner surface of the connector member, thereby immobilizing the connector.

The connector members are rigid structures adapted to link an associated anchoring assembly with one of the stabilizing rods. The stabilizing rods may be rigid or dynamic members shaped to form a spine-curvature-correcting and/or immobilizing path. Attaching each anchoring assembly, via connectors, to a stabilizing rod forces a patient's back into a surgeon-chosen shape. Stabilizing rods may be used singly, or in pairs, depending upon the type of correction required. The rods vary in size, but typically extend between at least two vertebrae.

Accordingly, it is an objective of the present invention to teach the use of a polyaxial pedicle screw system for posterior fixation having a common connector for use with different sized shanks and thread types, which lowers inventory requirements and provides the surgeon with a uniform connector.

It is another objective of the present invention to teach the use of a polyaxial pedicle screw having a biasing member to apply a force between the anchoring member and the connector member, the force facilitates installation by maintaining the connector component in an angular placement position as desired by the surgeon.

It is another objective of the present invention to teach the use of a polyaxial bone screw assembly having a thicker connector even when oversized anchoring screws are employed by use of a thread thru design of a lower connector, the upper connector need not be threaded providing a greater safety factor when a set screw fastener is employed by avoiding splaying.

Another objective of the present invention to teach the use of a polyaxial bone screw assembly that can allow for multiple rod connector member diameter sizes for use with a single sized connector assembly.

Still another objective of the present invention to teach the use of a retainer ring member for use in conjunction with a U-shaped saddle to obtain a three point fixation between a fastener set screw and the saddle.

Yet another objective of the present invention to teach the use of a polyaxial bone screw assembly that allows 60 degrees of conical polyaxial motion.

It is yet another objective of the present invention to provide a simple spinal fixation system having only a few components for use in assembly and limiting component parts needed during assembly by use of a common connector.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

FIG. 1 is a side view of the thread thru pedicle screw apparatus of the instant invention shown with an anchoring member at its permitted angular offset;

FIG. 2 is a side view of the thread thru pedicle screw apparatus shown with a large rod element;

FIG. 3 is a side view of the thread thru pedicle screw apparatus shown with a smaller rod element;

FIG. 7a is a top perspective view of the upper connector element;

FIG. 7b is a bottom perspective view of the upper connector element;

FIG. 7c is a side view of the upper connector element;

FIG. 7d is a top view of the upper connector element;

FIG. 7e is a bottom view of the upper connector element;

DETAILED DESCRIPTION OF THE PREFERRED EMBODIMENT

Figures 4, 5:
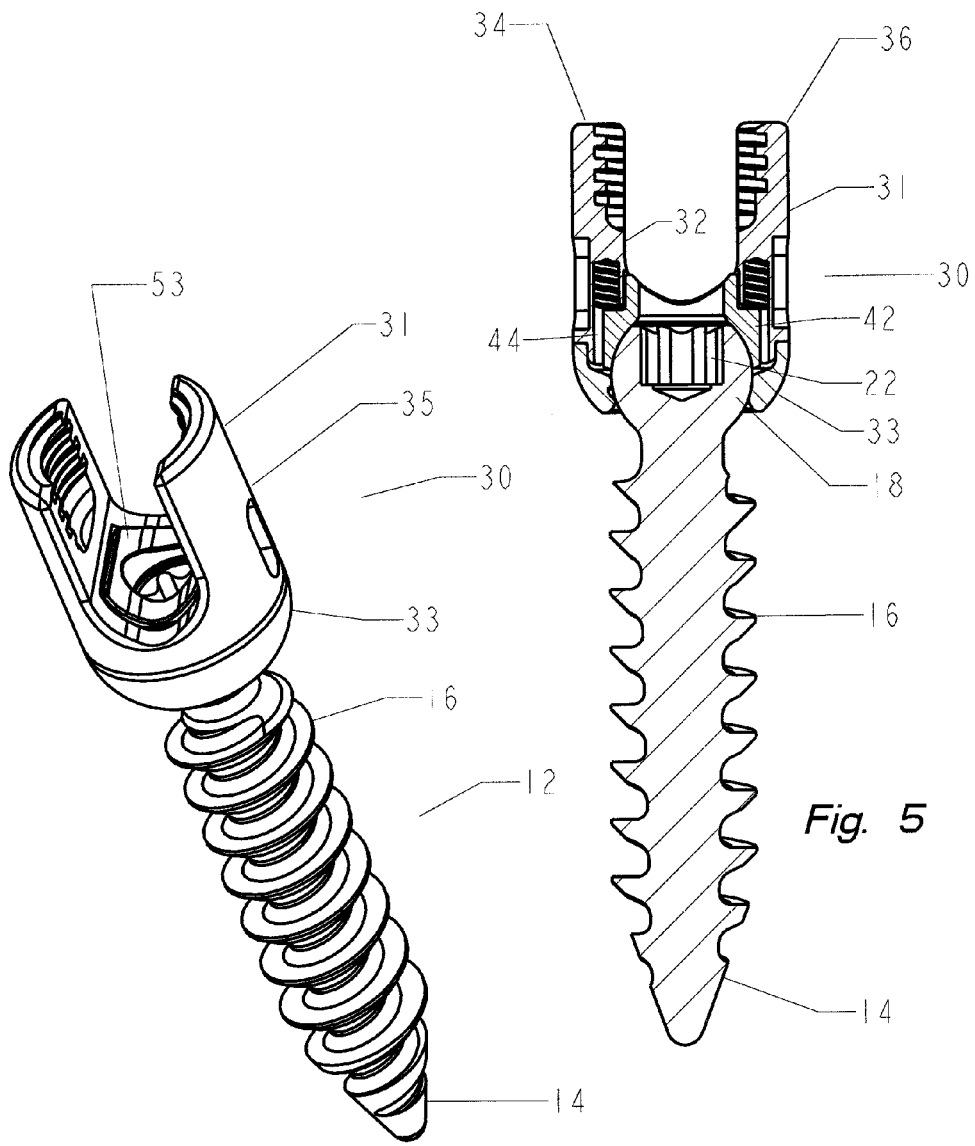
FIG. 4 is a perspective view of the thread thru pedicle screw apparatus without a rod or set screw.
FIG. 5 is a cross section view of the thread thru pedicle screw apparatus.
Figure 6:
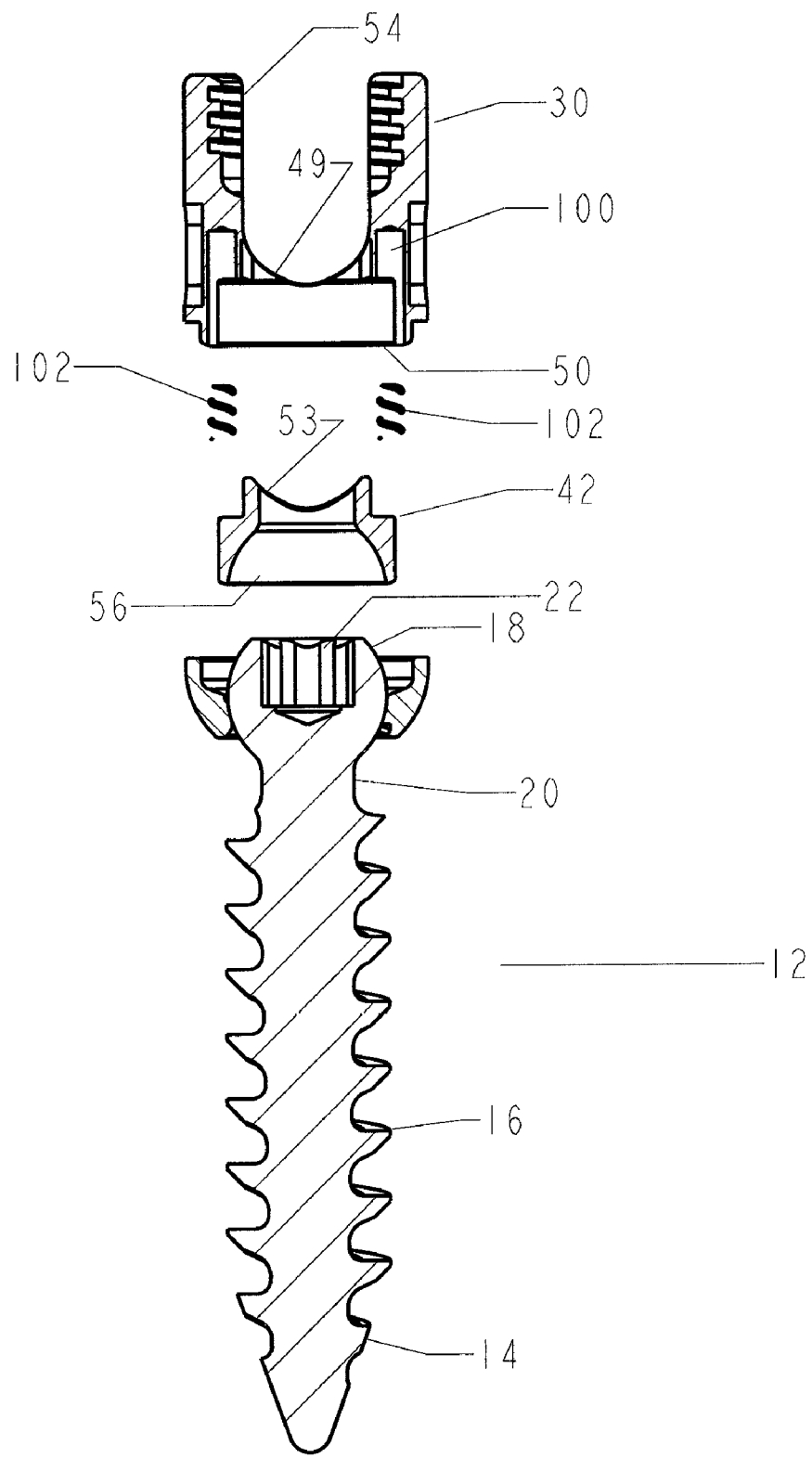
FIG. 6 is an exploded cross section view of the thread thru pedicle screw apparatus.
Figure 8A:
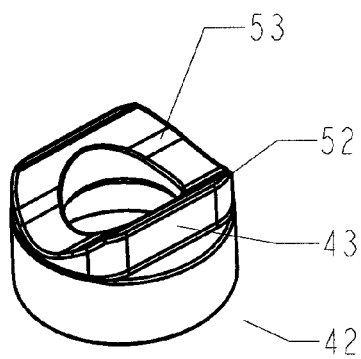
FIG. 8a is a top perspective view of the retainer ring element.
Figure 8C:
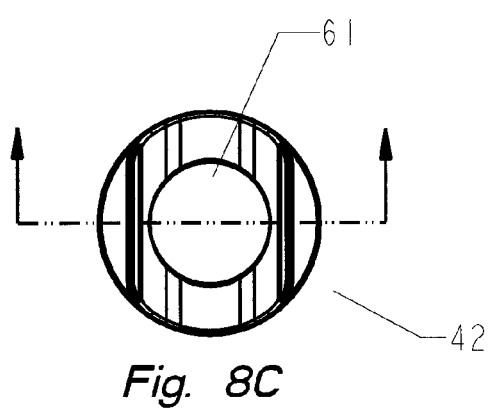
FIG. 8c is a top view of the retainer ring element.
Figure 8B:
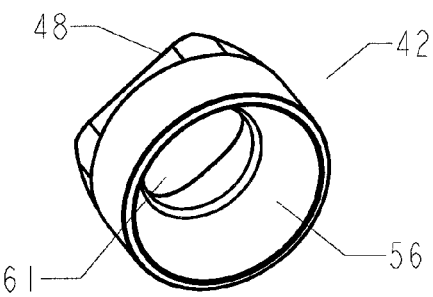
FIG. 8b is a bottom perspective view of the retainer ring element.
Figure 8D:
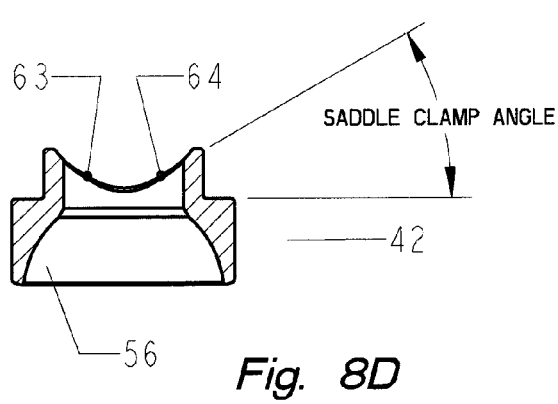
FIG. 8d is a sectional view of the retainer ring element.
Figure 9A:
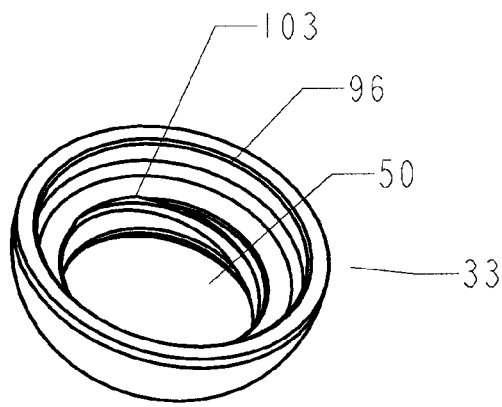
FIG. 9a is a top perspective view of the lower connector element.
Figure 9C:
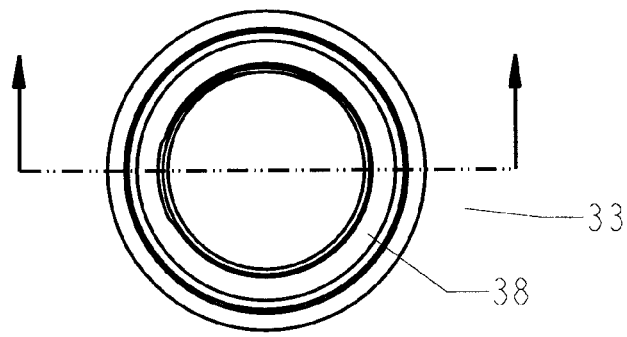
FIG. 9c is a top view of the lower connector element.
Figure 9B:
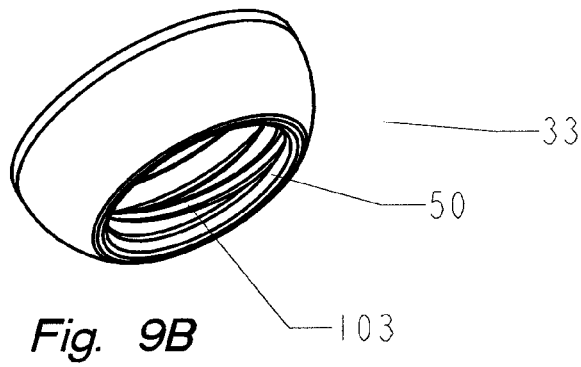
FIG. 9b is a bottom perspective view of the lower connector element.
Figure 9D:
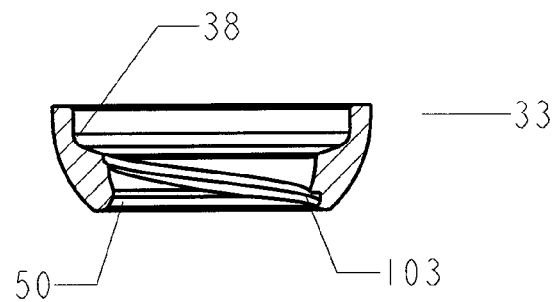
FIG. 9d is a sectional view of the retainer ring element of the lower connector element.
Figures 10A, 10B, 10C:
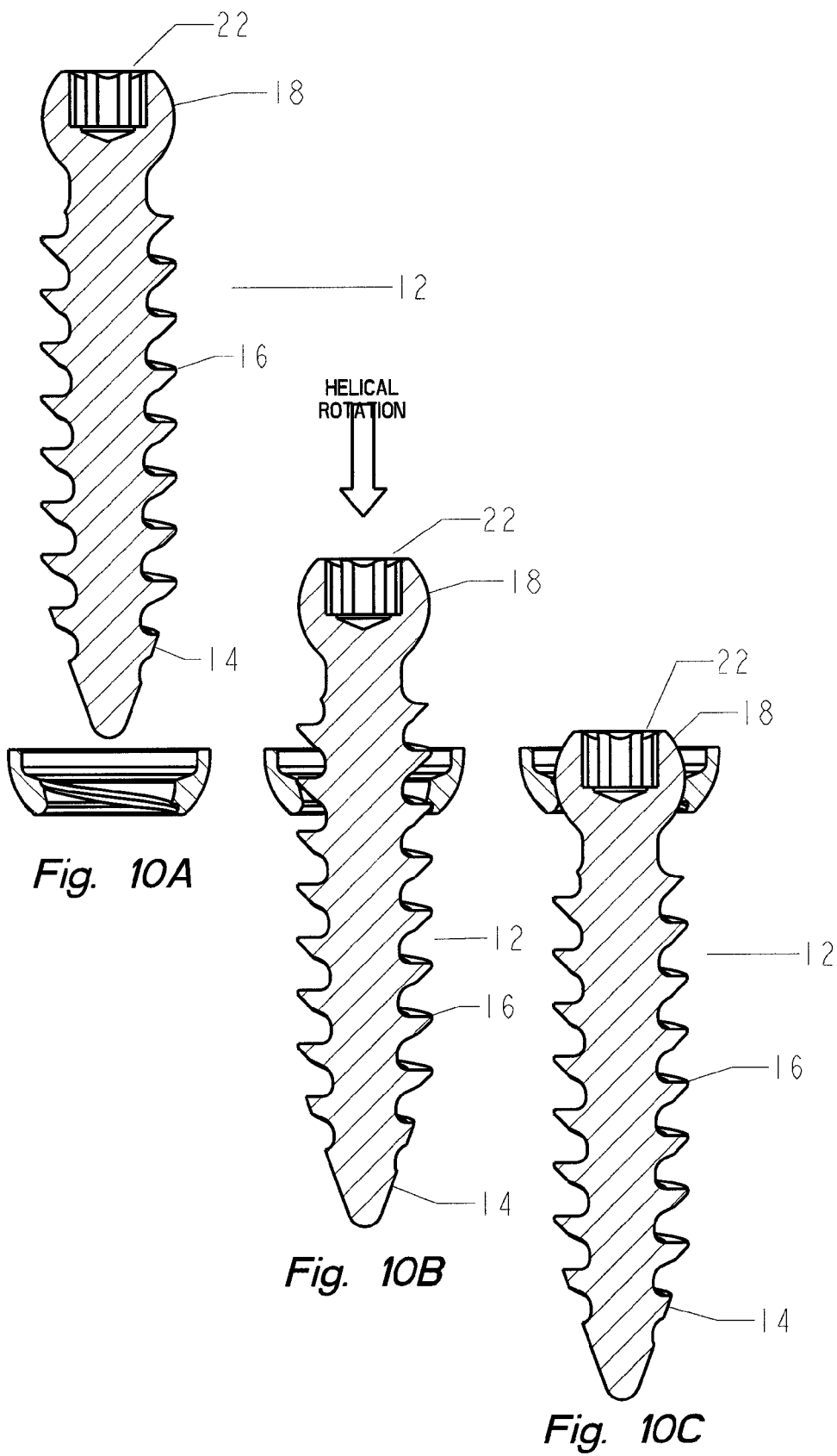
FIG. 10a is an exploded sectional view depicting the thread thru installation of the anchoring member to the lower connector element.
FIG. 10b is a partially assembled sectional view depicting the thread thru installation of the anchoring member to the lower connector element.
FIG. 10c is an assembled sectional view depicting the thread thru installation of the anchoring member to the lower connector element.
Figure 11:
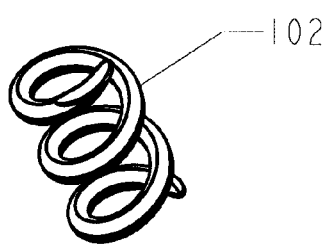
FIG. 11 is a perspective view of a spring biasing element.
Figure 12:
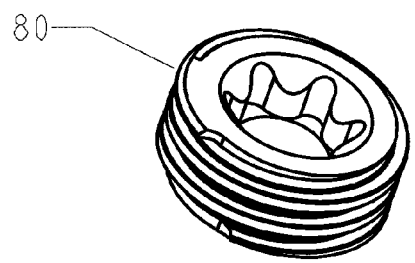
FIG. 12 is a perspective view of a set screw fastener element.
Figure 13:
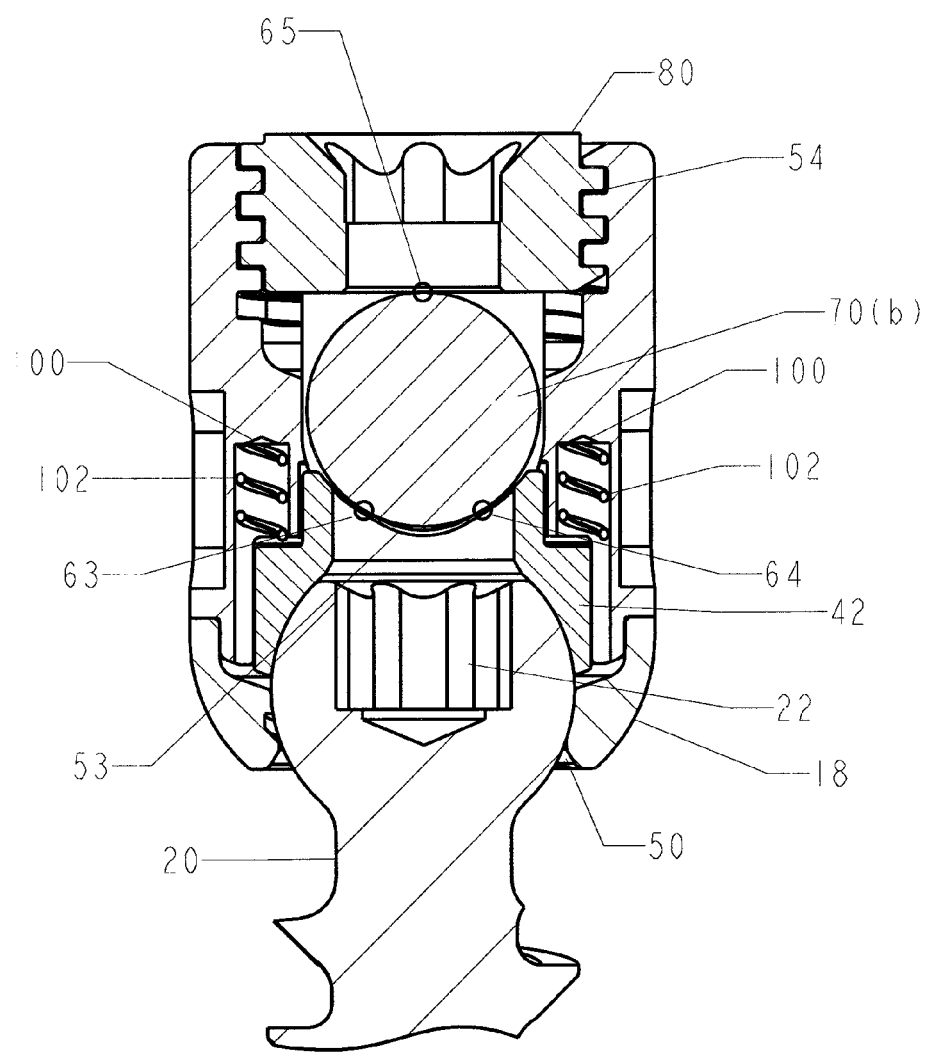
FIG. 13 is an enlarged cross sectional view of the connector assembly.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiments illustrated.

Referring generally to the Figures, disclosed is an exemplary embodiment of the thread thru polyaxial pedicle screw system for use in a spinal fixation system. The thread-thru pedicle screw system (10) is based on an anchoring member formed from a bone screw (12) including a shank (14) with at least one helical thread (16) formed along the length thereof. It is important to note that the proportions of the bone screw depicted are for illustrative purposes only and variations in the length of the shank, diameter of the screw, thread pitch, thread length, number of thread leads, shank induced compression and the like may be varied without departing from the scope of the invention. As will be further described later in this specification, unique to invention is the ability to use various shank widths and thread sizes with the same connector which reduces the manufacturing inventory. At the upper end (20) of the shank (14) is a ball shaped spherical connector (18) having a predetermined diameter. The diameter of the spherical connector (18) and the width of the shank (20) control the angular positioning (A) of about 60 degrees that the shank has of conical polyaxial motion in relation to the connector assembly (30). A driver receptacle (22) is located along the upper end (20) of the spherical connector for use in installing the bone screw by use of driving tool. It should be noted that the driving receptacle may be any shape, male or female, suitable for cooperation with a driving tool to rotate the bone screw into its final position.

The connector assembly (30) is U-shaped and includes an upper connector member (31), a lower connector member (33), and a retaining ring (42). The upper connector member includes a substantially circular side wall (32) divided by a pair of U-shaped openings (49) forming an upstanding first interior side wall (34) and second interior side wall (36). A portion of each said side wall is threaded (54) for receipt of a set screw (80). The connector assembly is sized to cooperate with the retaining ring (42) for receipt of various sized rod. FIG. 2 depicts a 6 mm rod (70a) within the connector member. FIG. 3 depicts a 5.5 mm rod (70b).

The outer side walls of the upper connector may include a plurality of recessed grooves (35). The grooves are constructed and arranged in a horizontal plane, as shown, and may also be placed in a vertical plane, not shown. The horizontal grooves further allow attachment of an extender tube (not shown). Extender tubes are well known in the art of minimally invasive spinal procedures. Vertical placed grooves provide a gripping surface that cooperates with a tool (not shown) to allow a physician to apply a counter torque to the connector member during tightening of the fastening member.

The upper connector member (31) preferably includes a shoulder (92) on the bottom surface thereof for location of the lower connector member (33) forming a socket area (44) for receipt of a retainer ring (42) there between. The socket area (44) is constructed and arranged to cooperate with the spherical ball connector on the bone screw and is further designed to prevent rotation of the retainer ring (42) thereby maintaining the saddle surface area in alignment with the U-shaped opening. Alignment is maintained by inset side walls (45, 46) which operate in conjunction with side walls (43, 48) of the retainer ring (42).

The lower connector member (33) also includes a shoulder (96) that is constructed and arranged to cooperate with shoulder (92) to maintain alignment of the two components. The lower connector member (33) includes a substantially spherical shaped receptacle (38) which operates in conjunction with the upper component member to house the retainer ring (42) used to engage the spherical ball (18). The shoulders (92) and (96) are utilized to align the components and the upper and lower connector members, once assembled the connector members are laser welded together. It should be noted that other suitable methods or techniques of attaching the upper and lower connector members together may be utilized without departing from the scope of the invention, such methods may include, but should not be limited to spot welding, threads, adhesives, pins swaging, solder, interference fits and suitable combinations thereof.

The retainer ring (42) is positioned within the lower receptacle (38) with an upper edge (52) positionable within the cavity formed by side wall (41); the retaining ring side wall (43) cooperates with side wall (41) of the cavity to prevent rotation of the retaining ring. The inner surface (56) of the retaining ring (42) has a spherical diameter and provides for self centering by engaging of the outer surface of the spherical connector (18). The upper surface (53) of the retaining ring (42) includes a concave cylindrical surface for cooperation with the connecting rod (70a or 70b). The cylindrical surface provides additional surface area for contact with the connecting rod and may include a knurled or otherwise modified surface finish adapted to enhance gripping power between the rod (70a or 70b) and the connecting assembly (30). The retaining ring (42) includes a biasing member to cause an applied force from the retaining ring (42) to the spherical ball (18). In the preferred embodiment the biasing member is a pair of coil springs (102) that are located to cooperate with spring pockets (100) positioned in the upper connector member to locate and contain coil springs (102). The coil springs (102) bias the retaining ring (42) towards the opening (50) of the lower receptacle (38). Once the anchoring member is secured to the bone, a rod (70a or 70b) is placed within the connector assembly fits within the U-shaped saddle (49) and is placed on the surface (53) of the retainer ring (42). The set screw (80) is threaded onto the threads (54) of the upper connector (31) wherein the rod (70a or 70b) forces the retainer ring (42) onto the spherical ball connector (18) locking the assembly into a fixed position. Alternatively the upper connector member can include the use of the well known fastener type wherein the upper connector member had an external thread and the fastener element would be a nut having internal threads.

The surface (53) of the retainer ring (42) includes a clamp angle that provides positive contact with the rod connection member along three points, point 1 (63) and point 2 (64) are from the shape of the clamp angle with the exact point position dependant upon the diameter of the connecting rod. A third point, point 3 (65) is supplied by the bottom of the set screw (80) creating three point securement when used with any diameter rod.

The thread-thru pedicle screw system (10) is constructed through the steps of selecting an anchoring member having a threaded shank (16) of an elected size for a particular installation. The shank may be small or large, the threads may be small or large, or any combination therebetween. A spherical connector (18) is of a common size allowing the use of a single sized lower connector element (33). The threaded shank (14) is inserted into the opening (50) of the lower connector member (33), the lower connector member having a socket (38) with a centrally disposed aperture which is constructed and arranged to allow the threaded shank to pass through. The lower connector member (33) includes a pass through thread (103) which allows the larger threaded shanks to pass through by matching the threaded shank with the pass through thread. In operation, the an oversized bone screw can be installed by use of a helical rotation wherein the bone screw is threaded through the member (33). The pass through thread (103) having a helical assembly groove to match the bone screw threads. The spherical connector (18) remains the same size and is situated in the socket (96), the design allowing a variety of anchor screws to be inventoried yet only one size connector assembly 30 needs to be inventoried.

Once the anchoring screw is positioned, the retainer ring is placed in the socket (96), the retainer ring (42) having a lower spherical surface (56) positionable along an upper surface of the spherical connector (18), the upper surface (53) of the retainer ring constructed and arranged to receive a connecting rod. A clearance aperture (61) allows passage of a driver for use in securing to the bone screw driver receptacle (22). Each of the coil springs (102) is seated within the upper connector (31) within the spring pockets (100). The upper connector member (31) is then coupled, or welded as previously mentioned, to the lower connector member (33) engaging the springs (102) to bias the retainer ring (42) against the spherical connection (18).

It should be noted that while the biasing member is illustrated as a pair of coil springs (102), any spring or resilient type member suitable for displacing the retaining ring may be utilized without departing from the scope of the invention. Such spring or resilient members may include, but should not be limited to, Belleville type springs, leaf springs, polymeric members and suitable combinations thereof.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A thread-thru pedicle screw system comprising:
   an anchoring member having a threaded shank and a spherical connector;
   a connecting assembly defined by a lower connector member coupled to an upper connector member, said lower connector member having a threaded aperture sized to allow only said threaded shank of said anchoring member to pass through and a socket for receipt of said spherical connector, said upper connector member having an opening for receipt of a connecting rod member and a bottom with at least one spring pocket formed therein;
   a retainer ring disposed between said lower connector member and said upper connector member, said retainer ring having a lower spherical surface positionable along an upper surface of said spherical connector;
   at least one biasing member having a first end positionable in said spring pocket of said upper connector member and a second end cooperating with an upper surface of said retainer ring, said biasing member positioned between said retainer ring and said upper connector member; and
   a fastener element securable to said upper connector member for engaging of said connecting rod member;
   wherein said connecting rod member is placed in said opening of said upper connector member and said fastener element is secured thereto for engaging the connecting rod member which engages said retainer ring whereby said retainer ring locks said connecting assembly in a fixed position in relation to said anchoring member.

2. The thread-thru pedicle screw system of claim 1 wherein said opening of said upper connector member is U-shaped for receipt of said connecting rod member.

3. The thread-thru pedicle screw system of claim 2 wherein said retaining ring extends into said U-shaped opening.

4. The thread-thru pedicle screw system of claim 1 wherein said retaining ring includes a cylindrically concave upper surface for cooperation with said connecting rod member.

5. The thread-thru pedicle screw system of claim 4 wherein said cylindrically concave upper surface of said retainer ring is constructed and arranged to engage a connecting rod member from about 5.5 mm diameter to about 6.0 mm, said cylindrically concave upper surface having a clamp angle including a pair of diverging substantially planar surfaces extending into said opening of said upper connector member.

6. The thread-thru pedicle screw system of claim 1 wherein said shank may include at least one helical thread.

7. The thread-thru pedicle screw system of claim 1 wherein said upper connecting member includes an internal thread and said fastener element is further defined as a set screw.

8. The thread-thru pedicle screw system of claim 1 wherein said upper connector member includes an external thread and said fastener element is further defined as a nut having internal threads.

9. The thread-thru pedicle screw system of claim 1 wherein said biasing member is further defined as a coil spring.

10. A thread-thru pedicle screw system comprising:
    an anchoring member having a threaded shank and a spherical connector;
    a connecting assembly defined by a lower connector member coupled to a U-shaped upper connector member, said lower connector member having a threaded aperture sized to allow only said threaded shank of said anchoring member to pass through and a socket for receipt of said spherical connector, said U-shaped upper connector member forming an opening for receipt of a connecting rod member and includes a bottom with at least one spring pocket formed therein;
    a retainer ring disposed between said lower connector member and said upper connector member, said retainer ring having a cylindrically concave upper surface for placement of said connecting rod member and a lower spherical surface positionable along an upper surface of said spherical connector;

at least one coil spring having a first end positionable in said spring pocket of said upper connector member and a second end cooperating with an upper surface of said retainer ring, said coil spring positioned between said retainer ring and said upper connector member; and a fastener element securable to said upper connector member for engaging of said connecting rod member;

wherein said connecting rod member is placed in said opening of said U-shaped upper connector member and said fastener element is secured thereto for engaging the connecting rod member which engages said retainer ring whereby said retainer ring locks said connecting assembly in a fixed position in relation to said anchoring member.

11. The thread-thru pedicle screw system of claim 10 wherein said cylindrically concave upper surface of said retainer ring is constructed and arranged to engage a connecting rod member from about 5.5 mm diameter to about 6.0 mm, said cylindrically concave upper surface having a clamp angle including a pair of diverging substantially planar surfaces extending into said opening of said U-shaped upper connector member.

12. The thread-thru pedicle screw system of claim 10 wherein said upper retaining ring extends into said U-shaped opening.

13. The thread-thru pedicle screw system of claim 10 wherein said shank may include at least one helical thread.

14. The thread-thru pedicle screw system of claim 10 wherein said upper connecting member includes an internal thread and said fastener element is further defined as a set screw.

15. The thread-thru pedicle screw system of claim 10 wherein said upper connector member includes an external thread and said fastener element is further defined as a nut having internal threads.

16. A method of constructing a thread-thru pedicle screw system constructed through the steps comprising:

forming a connecting assembly defined by a lower connector member having a socket with a threaded aperture and an upper connector member having an opening for receipt of a connecting rod member and a bottom with at least one spring pocket formed therein;

selecting a one piece anchoring member having a threaded shank of an elected size and a spherical connector;

inserting said threaded shank into said threaded aperture of said lower connector member, said aperture constructed and arranged to allow only said threaded shank to pass through with said socket receiving said spherical connector;

positioning a retainer ring between said lower connector member and said upper connector member, said retainer ring having a lower spherical surface positionable along an upper surface of said spherical connector and an upper surface constructed and arranged to receive a connecting rod;

placing a biasing member between said upper connector member and an upper surface of said retainer ring, said biasing member having a first end positionable in said spring pocket and a second end cooperating with said upper surface of said retainer ring;

coupling said upper connector member to said lower connector member, said biasing member maintaining said anchoring member in an operator oriented position.

* * * * *